(12) United States Patent
Mayerson

(10) Patent No.: US 12,390,333 B2
(45) Date of Patent: Aug. 19, 2025

(54) SUTURE HOLE GEOMETRY AND METHODS FOR ATTACHING TISSUE TO ORTHOPEDIC IMPLANTS

(71) Applicant: Onkos Surgical, Inc., Parsippany, NJ (US)

(72) Inventor: Joel Mayerson, Columbus, OH (US)

(73) Assignee: ONKOS SURGICAL, INC., Parsippany, NJ (US)

( * ) Notice: Subject to any disclaimer, the term of this patent is extended or adjusted under 35 U.S.C. 154(b) by 98 days.

(21) Appl. No.: 17/531,717

(22) Filed: Nov. 20, 2021

(65) Prior Publication Data

US 2022/0160510 A1 May 26, 2022

Related U.S. Application Data

(60) Provisional application No. 63/116,601, filed on Nov. 20, 2020.

(51) Int. Cl.
| | |
|---|---|
| *A61F 2/30* | (2006.01) |
| *A61B 17/04* | (2006.01) |
| *A61F 2/36* | (2006.01) |
| *A61F 2/38* | (2006.01) |

(52) U.S. Cl.
CPC ...... *A61F 2/30771* (2013.01); *A61B 17/0401* (2013.01); *A61F 2/3607* (2013.01); *A61F 2/389* (2013.01); *A61B 2017/0414* (2013.01); *A61F 2002/3006* (2013.01); *A61F 2002/30784* (2013.01); *A61F 2002/30827* (2013.01)

(58) Field of Classification Search
CPC ...... A61F 2002/3822; A61F 2002/3694; A61F 2002/30461; A61F 2/30771; A61F 2/3607; A61F 2/389; A61F 2002/3006; A61F 2002/30784; A61F 2002/30827; A61F 2/36; A61F 2/3609; A61F 2002/3613; A61F 2002/3627
See application file for complete search history.

(56) References Cited

U.S. PATENT DOCUMENTS

| | | | |
|---|---|---|---|
| 5,458,653 A * | 10/1995 | Davidson | A61L 27/34 623/23.36 |
| 5,725,557 A | 3/1998 | Gatturna et al. | |
| 6,558,425 B2 | 5/2003 | Rockwood, Jr. | |
| 8,177,849 B2 | 5/2012 | Meyers et al. | |
| 8,715,356 B2 | 5/2014 | Porter et al. | |
| 9,724,212 B2 | 8/2017 | Lacraz | |
| 9,833,326 B2 | 12/2017 | Porter et al. | |
| 10,010,424 B2 * | 7/2018 | Ekelund | A61F 2/30728 |

(Continued)

*Primary Examiner* — Christopher D. Prone
(74) *Attorney, Agent, or Firm* — Corner Counsel, LLC

(57) ABSTRACT

Orthopedic implants and related surgical methods for using same. The implants have suture bore geometries that facilitate performance of the surgical methods, thereby providing for improved optimal biomechanical force application in various anatomies. The implants include suture bores that have an angled/diagonal, or skewed, orientation within the anatomical planes (lateral/sagittal and frontal/coronal). The suture bores have the skewed orientation so that the adjacent soft tissues (i.e., tendons or ligaments) can be advanced via the suture therethrough in superior-inferior and inferior-superior directions. Openings, or holes, at the ends of the suture bores are configured to approximate the adjacent associated soft tissue to the implant.

16 Claims, 8 Drawing Sheets

(56) References Cited

U.S. PATENT DOCUMENTS

| | | |
|---|---|---|
| 10,383,734 B2 | 8/2019 | Ekelund et al. |
| 10,485,669 B2 | 11/2019 | Maale |
| 2007/0129809 A1 | 6/2007 | Meridew et al. |
| 2012/0271349 A1 | 10/2012 | Lederman et al. |
| 2017/0079802 A1* | 3/2017 | Porter ..................... A61F 2/32 |
| 2018/0280146 A1 | 10/2018 | Yadav et al. |

* cited by examiner

SUTURE HOLE GEOMETRY AND METHODS FOR ATTACHING TISSUE TO ORTHOPEDIC IMPLANTS

RELATED APPLICATION

This application claims priority to U.S. Provisional Patent Application Ser. No. 63/116,601, filed Nov. 20, 2020, the disclosure of which is hereby incorporated by reference in its entirety.

FIELD OF THE INVENTION

Embodiments of the invention relates generally to orthopedic implants (e.g., hip and knee replacement implants) for use in the surgical repair of a defect or disease in a patient's bone/joints, and more particularly, to orthopedic implants configured for attachment to the patient's soft tissue adjacent the bone/joint, and related surgical methods involving same.

BACKGROUND OF THE INVENTION

Orthopedic implants (e.g., hip and knee replacement implants) are used to repair bone and joint defects and are surgically attached to a patient's soft tissues adjacent such defects.

Typically, suture bores/holes for attaching such implants are oriented perpendicular to anatomical planes (lateral/sagittal and frontal/coronal). More particularly, known suture attachment bores in implants only pull and hold tissue/bone directly perpendicular to the surface of the implant. However, it is desirable to provide suture bore geometries and methods for attaching soft tissue to orthopedic implants in improved, optimal ways and orientations intraoperatively, and for improved optimal biomechanical force application in various anatomies.

SUMMARY OF THE INVENTION

Disclosed herein is an implant comprising a superior end; an inferior end opposite the superior end; a longitudinal axis extending between the superior and inferior ends; a first side extending between the superior and inferior ends; a second side opposite the first side and extending between the superior and inferior ends; an anterior surface extending between the superior and inferior ends; a posterior surface opposite the anterior surface and extending between the superior and inferior ends; a first suture hole proximate the superior end; a second suture hole between the first suture hole and the inferior end; and a first suture bore formed between the first and second suture holes and extending at a first acute angle with the longitudinal axis in the frontal plane, and extending at a second acute angle with the longitudinal axis in the lateral plane; a third suture hole proximate the superior end and the second suture hole; a fourth suture hole between the third suture hole and the inferior end; and a second suture bore formed between the third and fourth suture holes and extending at the first acute angle with the longitudinal axis in the frontal plane, and extending at the second acute angle with the longitudinal axis in the lateral plane.

Further disclosed herein is proximal tibia implant comprising: a superior end; an inferior end opposite the superior end; a longitudinal axis extending between the superior and inferior ends; a first side extending between the superior and inferior ends; a second side opposite the medial side and extending between the superior and inferior ends; an anterior surface extending between the superior and inferior ends; a posterior surface opposite the anterior surface and extending between the superior and inferior ends; a first suture hole formed in the first side between the superior and inferior ends; a second suture hole formed in the anterior surface proximate the superior end and first side; a first suture bore formed between the first and second suture holes and extending at a first acute angle with the longitudinal axis in the frontal plane, and extending at a second acute angle with the longitudinal axis in the lateral plane; a third suture hole formed in the anterior surface proximate the superior end and second side; a fourth suture hole formed in the second side between the superior and inferior ends; and a second bore formed between the third and fourth suture holes and extending at the first acute angle with the longitudinal axis in the frontal plane, and extending at the second acute angle with the longitudinal axis in the lateral plane.

Still further disclosed herein is proximal femur implant comprising: a superior end; an inferior end opposite the superior end; a longitudinal axis extending between the superior and inferior ends; a medial side extending between the superior and inferior ends; a lateral side opposite the medial side and extending between the superior and inferior ends; an anterior surface extending between the superior and inferior ends; a posterior surface opposite the anterior surface and extending between the superior and inferior ends; a first suture hole is formed in the posterior surface between the superior and inferior ends; a second suture hole formed in the lateral side proximate the superior end; a first suture bore formed between the first and second suture holes and extending at a first acute angle with the longitudinal axis in the frontal plane, and extending at a second acute angle with the longitudinal axis in the lateral plane; a third suture hole formed in the lateral side proximate the superior end; a fourth suture hole formed in the anterior surface between the superior and inferior ends.

Also disclosed herein is a method for attaching an implant to a patient's soft tissue, the method comprising the steps of (1) positioning an implant adjacent the patient's soft tissue, the implant having a superior end, an inferior end opposite the superior end, a longitudinal axis extending between the superior and inferior ends, a first side extending between the superior and inferior ends, a second side opposite the first side and extending between the superior and inferior ends, an anterior surface extending between the superior and inferior ends, a posterior surface opposite the anterior surface and extending between the superior and inferior ends, a first suture hole in the first side, a second suture hole in the anterior surface, proximate the superior end, a first bore formed between the first and second suture holes, the first bore extending at a first angle from the longitudinal axis, a third suture hole in the anterior surface, proximate the superior end, a fourth suture hole in the second side, and a second bore formed between the third and fourth suture holes, the second bore extending at a second angle from the longitudinal axis, wherein the second angle is opposite the first angle; (2) providing a suture having a first end and a second end opposite the first end; (3) directing the first end of the suture through the first suture hole, the first bore, and the second suture hole; (4) inserting the first end of the suture through a first portion of the patient's soft tissue adjacent the anterior surface of the implant; (5) inserting the first end of the suture through a second portion of the patient's soft tissue adjacent the first portion; (6) directing the first end of the suture through the third suture hole, the second bore, and the fourth suture hole, until the first end of the suture is proximate the second side of the implant, and the second end of the suture is proximate the first side of the implant; (7) pulling the patient's soft tissue towards the anterior surface of the implant; and (8) tying the first and second ends of the suture proximate the anterior surface of the implant to secure the implant to the patient's soft tissue.

Aligning the suture bores in orthopedic implants according to the present invention creates mechanical advantages to advance and manipulate the patient's anatomy (i.e., soft tissue) to the ideal anchorage location on the implant, which allows for more optimal biomechanical apposition and reconstruction of the bone/joint and adjacent soft tissue.

This Summary of the Invention is neither intended nor should it be construed as being representative of the full extent and scope of the present disclosure. The present disclosure is set forth in various levels of detail in the Summary of the Invention as well as in the attached drawings and the Detailed Description of the Invention, and no limitation as to the scope of the present disclosure is intended by either the inclusion or non-inclusion of elements, components, etc. in this Summary of the Invention. Additional aspects of the present disclosure will become more readily apparent from the Detailed Description, particularly when taken together with the drawings.

The above-described benefits, embodiments, and/or characterizations are not necessarily complete or exhaustive, and in particular, as to the patentable subject matter disclosed herein. Other benefits, embodiments, and/or characterizations of the present disclosure are possible utilizing, alone or in combination, as set forth above and/or described in the accompanying figures and/or in the description herein below. However, the Detailed Description of the Invention, the drawing figures, and the exemplary claim set forth herein, taken in conjunction with this Summary of the Invention, define the invention.

BRIEF DESCRIPTION OF THE FIGURES

The accompanying figures, which are incorporated in and constitute a part of the specification, illustrate preferred embodiments of the invention and, together with the description, serve to explain the objects, advantages, and principles of the invention. Embodiments of the invention are in no way limited by the following figures.

DETAILED DESCRIPTION OF THE INVENTION

The present invention includes orthopedic implants and related surgical methods for using same. As discussed further below, the implants are configured so that a surgeon performing a joint replacement (or similar) procedure using the implants can advance adjacent associated tissue (i.e., tendons and/or ligaments) in a superior-to-inferior and inferior-to-superior directions, which are generally parallel to and/or aligned with a line of action of such tissue. The tissue can thereby be restored to its approximate original anatomical position after being affixed to the implant.

Figure 1A:
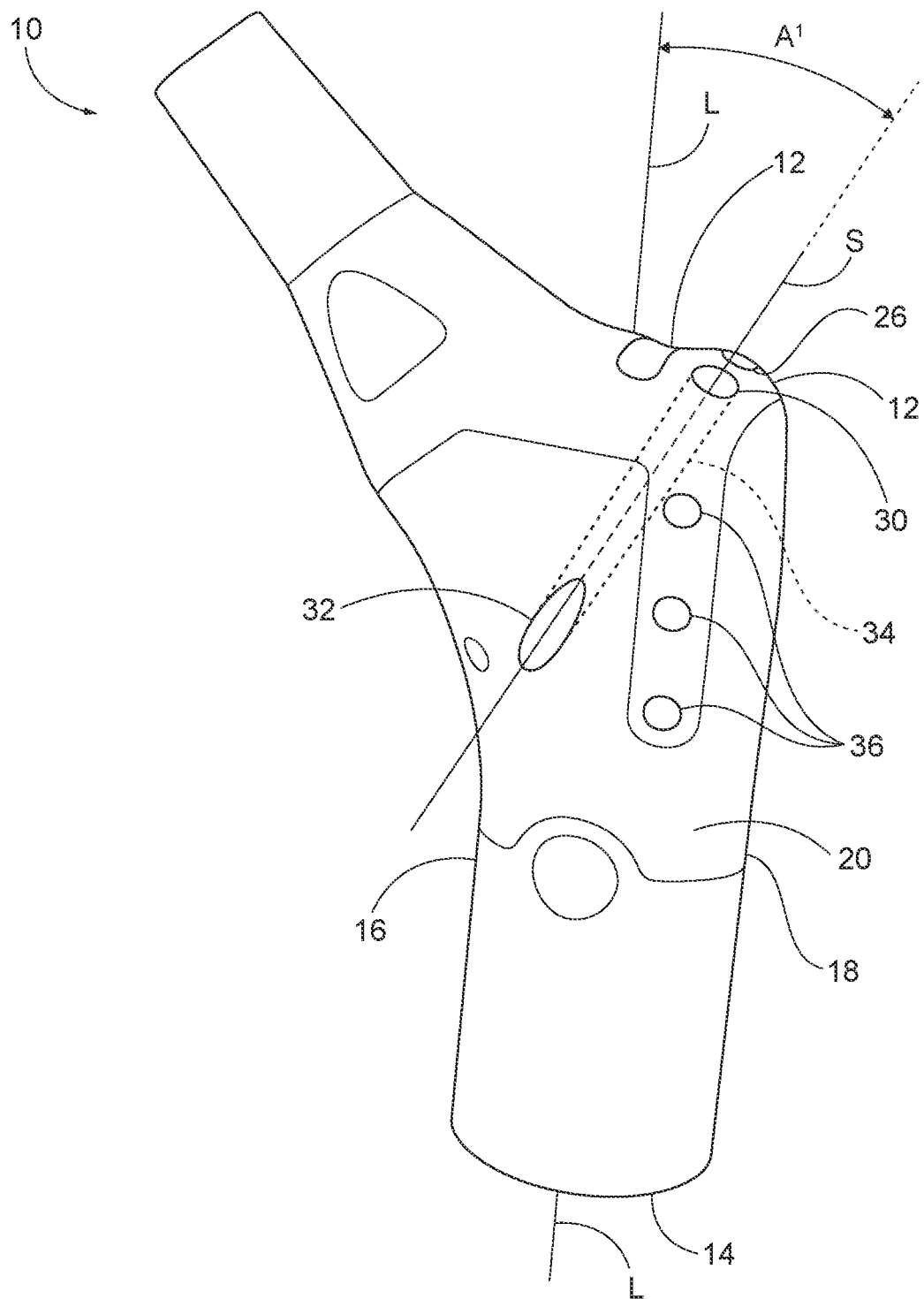
FIG. 1A is an anterolateral top perspective view of a proximal femur implant according to a first embodiment of the present invention.
Figure 1B:
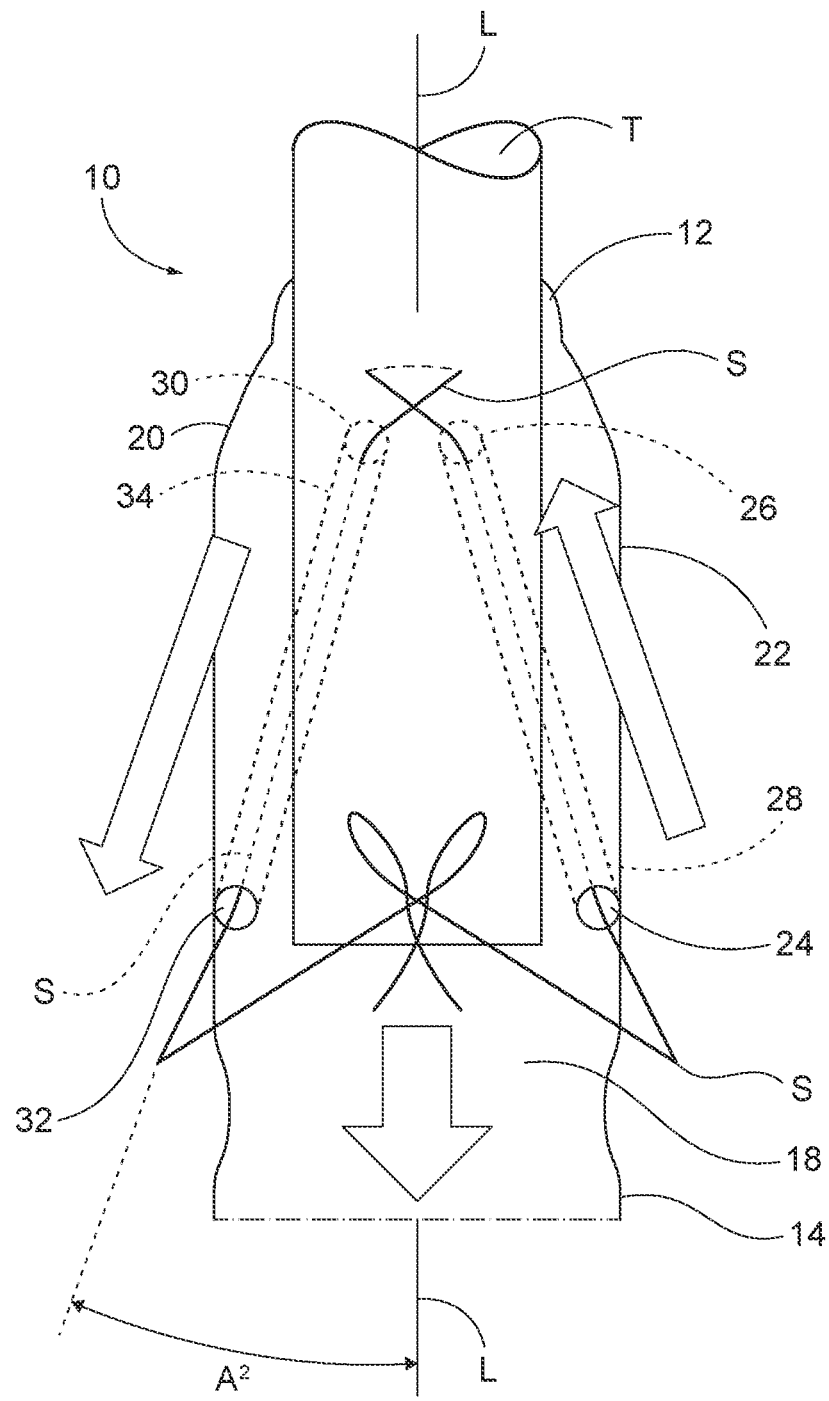
FIG. 1B is a lateral side view of the implant of FIG. 1A, looking medially, with a schematic representation of a surgical method according to an embodiment of the present invention.

Reference is made to FIGS. 1A and 1B, which illustrate a proximal femur implant 10 according to a first embodiment, and a related surgical method for using same. The implant illustrated in FIGS. 1A and 1B is for a patient's left proximal femur and the implant for a right proximal femur, while not shown, is a mirror-image thereof. As illustrated in FIGS. 1A and 1B and further discussed below, the implant 10 includes suture bores 28, 34 that have an angled/diagonal, or skewed, orientation within the anatomical planes (lateral/sagittal and frontal/coronal). The suture bores have the skewed orientation so that the adjacent soft tissues (i.e., tendons or ligaments) can be advanced via the suture therethrough in superior-inferior and inferior-superior directions. Openings, or holes, at the ends of the suture bores are configured to approximate the adjacent associated soft tissue to the implant.

With continued reference to FIGS. 1A and 1B, the proximal femur implant 10 includes a superior end 12, an inferior end 14 opposite the superior end 12, and a longitudinal axis L extending between the superior and inferior ends 12, 14. The implant 10 further includes a first, or medial, side 16 extending between the superior and inferior ends 12, 14, and a second, or lateral, side 18 opposite the first side 16 and extending between the superior and inferior ends 12, 14. An anterior surface 20 extends between the superior and inferior ends 12, 14, and a posterior surface 22 extends between the superior and inferior ends 12, 14, opposite the anterior surface 20.

The proximal femur implant 10 includes a plurality of suture holes. A first suture hole 24 is formed in the posterior surface 22 of the implant 10 between the superior and inferior ends 12, 14, and a second suture hole 26 is formed in the lateral side 18 of the implant 10 proximate the superior end 12. A first suture bore 28 is formed between the first and second suture holes 24, 26 and extends at a first acute angle $A_1$ with the longitudinal axis L in the frontal/coronal plane, and extends at a second acute angle $A_2$ with the longitudinal axis L in the lateral/sagittal plane. The implant 10 further includes a third suture hole 30 formed in the lateral side 18 proximate the superior end 12, and a fourth suture hole 32 is formed in the anterior surface 20 between the superior and inferior ends 12, 14. A second suture bore 34 is formed between the third and fourth suture holes 30, 32 and extends at the first acute angle $A_1$ with the longitudinal axis L in the frontal/coronal plane (see FIG. 1A, in which an imaginary dashed line extends from the second suture bore 34 to help illustrate this angle), and extends at the second acute angle $A_2$ with the longitudinal axis L in the lateral/sagittal plane (see FIG. 1B, in which an imaginary dashed line extends from the second suture bore 34 to help illustrate this angle).

In various embodiments, the first acute angle $A_1$ and second acute angle $A_2$ both range from 0° to 60° or from 10° to 40°. In a preferred embodiment, both the first acute angle $A_1$ and second acute angle $A_2$ range from 15° to 30°. In a more preferred embodiment, the first acute angle $A_1$ is 25°, and the second acute angle $A_2$ is 20°. The first acute angle $A_1$ and second acute angle $A_2$ are determined according to two criteria, namely, (1) an angle measurement that facilitates close alignment to the line of action of the soft tissue, and (2) an angle measurement that facilitates fitting the suture bore between other existing holes/features in the implant to avoid interference between the holes/features.

In the embodiments shown in FIGS. 1A and 1B the suture bores 28 and 34 have a diagonal, or skewed, orientation within the anatomical planes (lateral/sagittal and frontal/coronal). Other bore orientations (e.g., straight) are also possible and included in the scope of the invention. In various embodiments, the first and second bores 28, 34 can be curved if the implant 10 is cast or 3D-printed.

In various embodiments, the implant 10 includes additional suture bores. In some embodiments, one or more suture bores 36 extend between the anterior surface 20 and posterior surface 22. The suture bores 36 are used to secure (i.e., clamp) soft tissue (i.e., tendons or ligaments) against ingrowth/ongrowth surface(s) of the implant 10.

As illustrated in FIG. 1B, an exemplary surgical attachment method for securing the proximal femur implant 10 within a patient includes the steps of (1) inserting the suture S up through the first suture hole 24 and the first bore 28 (see arrow pointing at an upward angle); (2) urging the suture S out of the second suture hole 26 so that the suture S is positioned proximate the adjacent soft tissue T (e.g., a tendon or ligament); (3) cross-stitching the suture S through and behind the adjacent soft tissue T; (4) inserting the suture S down through the third suture hole 30 and the second bore 34 (see arrow pointing at a downward angle); (5) urging the suture S out of the fourth suture hole 32; and (6) pulling the adjacent soft tissue T down (see arrow pointing straight down) and tying the suture S off proximate the second/lateral side 18 of the proximal femur implant 10. In various alternate embodiments, the suture S may be tied off at other locations instead of the lateral side. In various embodiments, the suture S may be reversed and run back through the bore(s) and soft tissue T a second time, and any number of additional times, to provide additional anchorage for the implant 10. In various embodiments, the order in which these steps are performed may vary. Other modifications of the method by a surgeon are also envisioned.

Figure 2A:
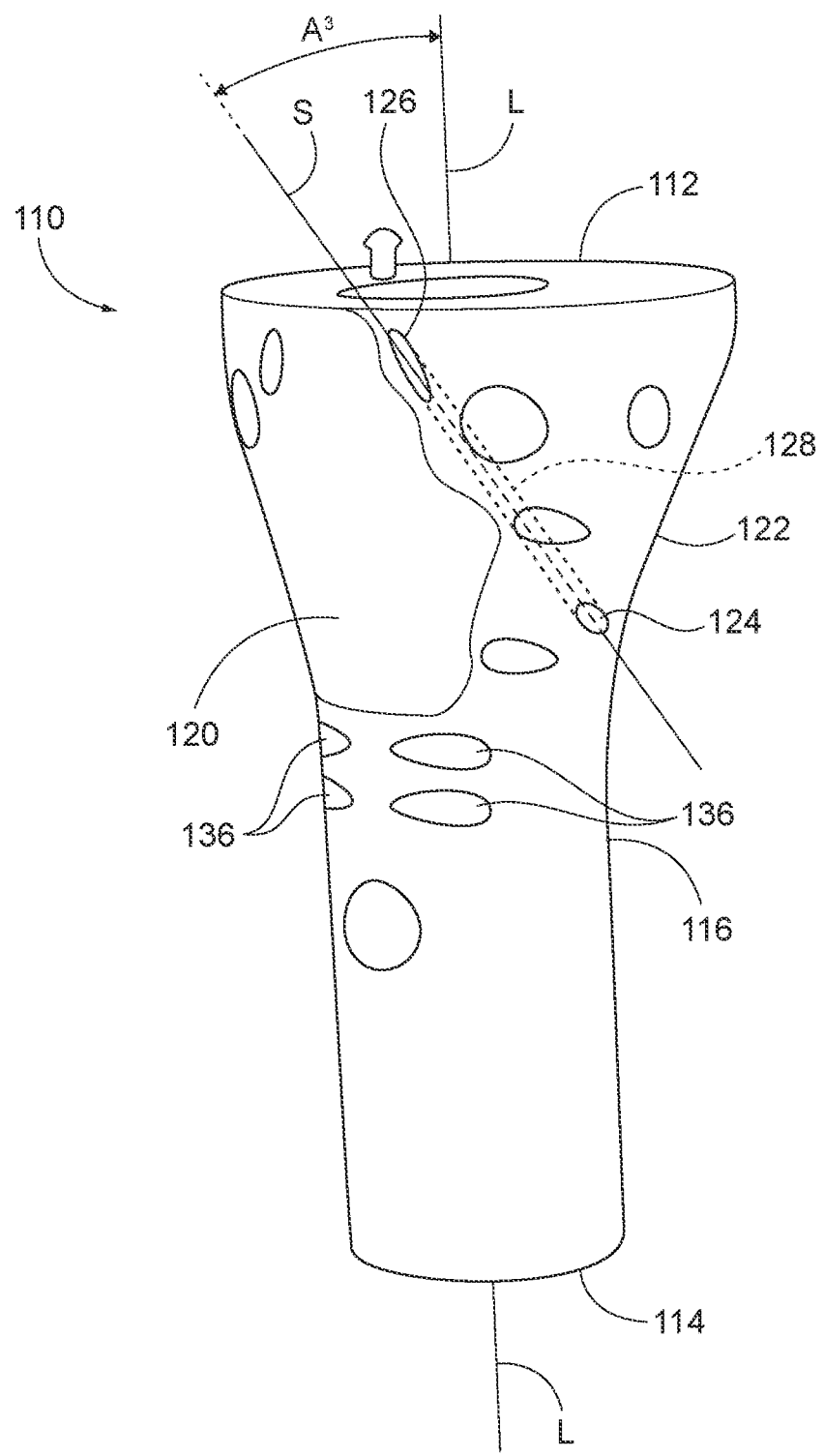
FIG. 2A is an anterolateral top perspective view of a proximal tibia implant according to a second embodiment of the present invention.
Figure 2B:
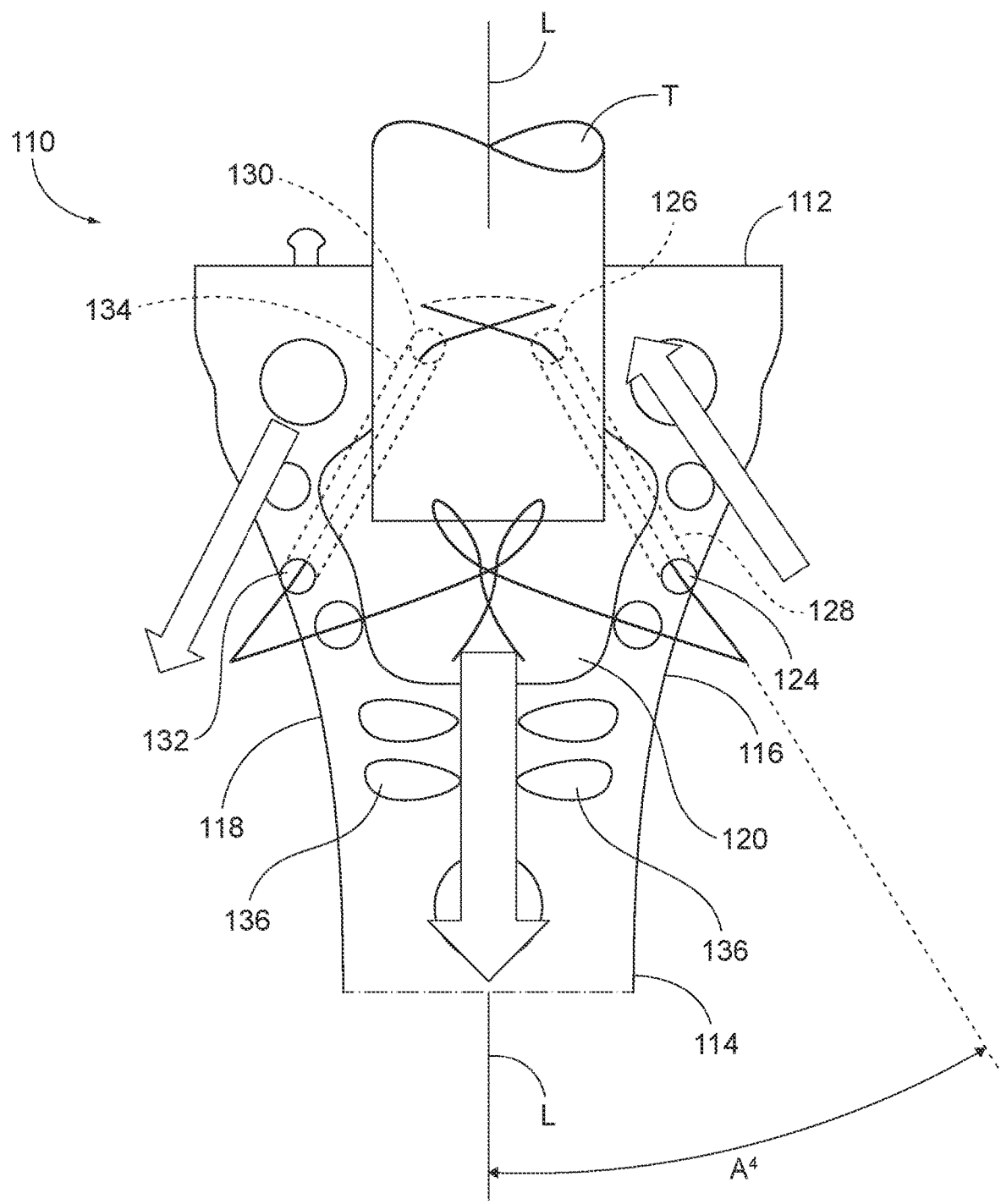
FIG. 2B is an anterior view of the implant of FIG. 2A, looking posteriorly, with a schematic representation of a surgical method according to an embodiment of the present invention
Figure 3:
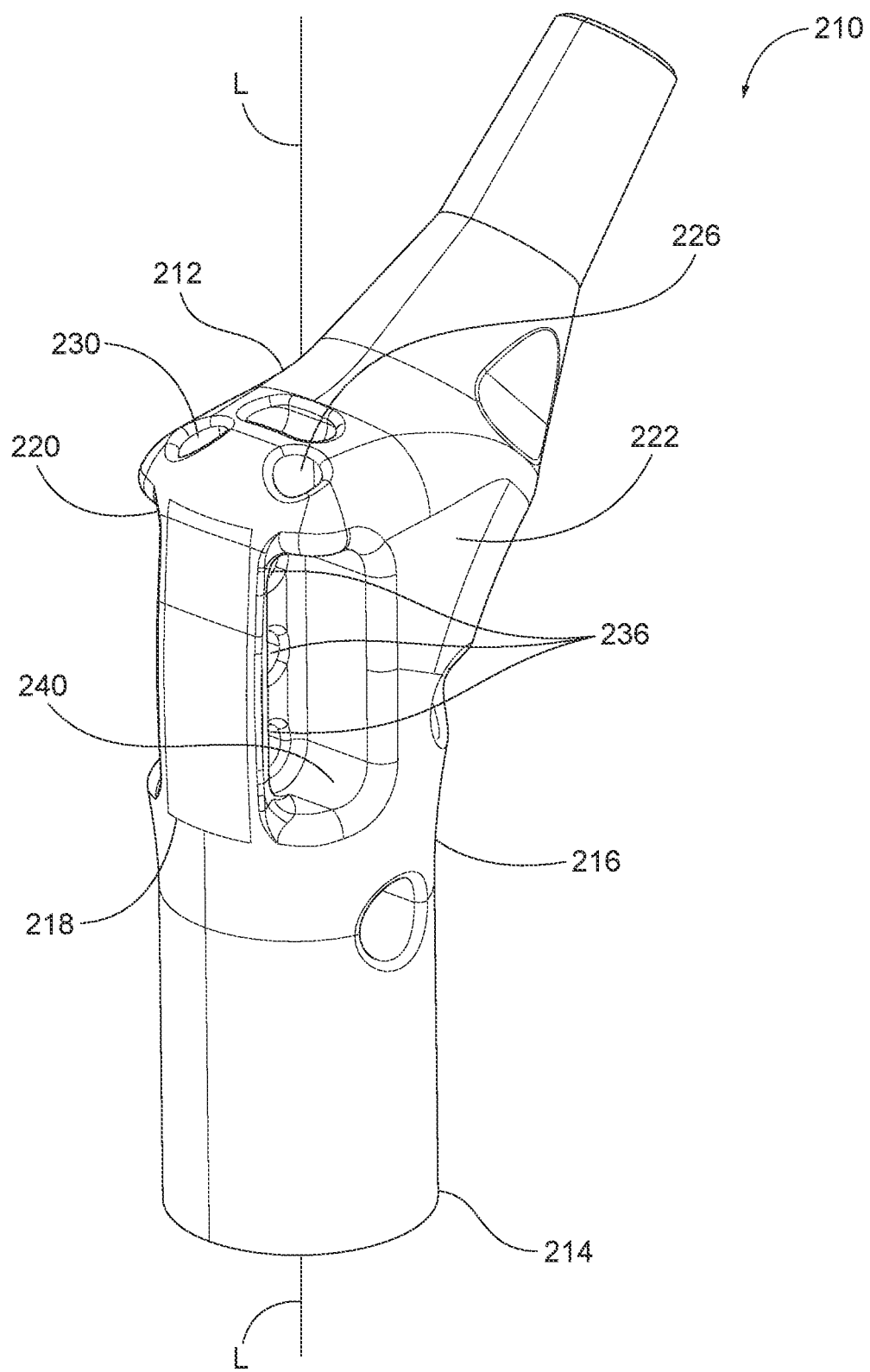
FIG. 3 is an anterolateral top perspective view of a proximal femur implant according to a third embodiment of the present invention.
Figure 4:
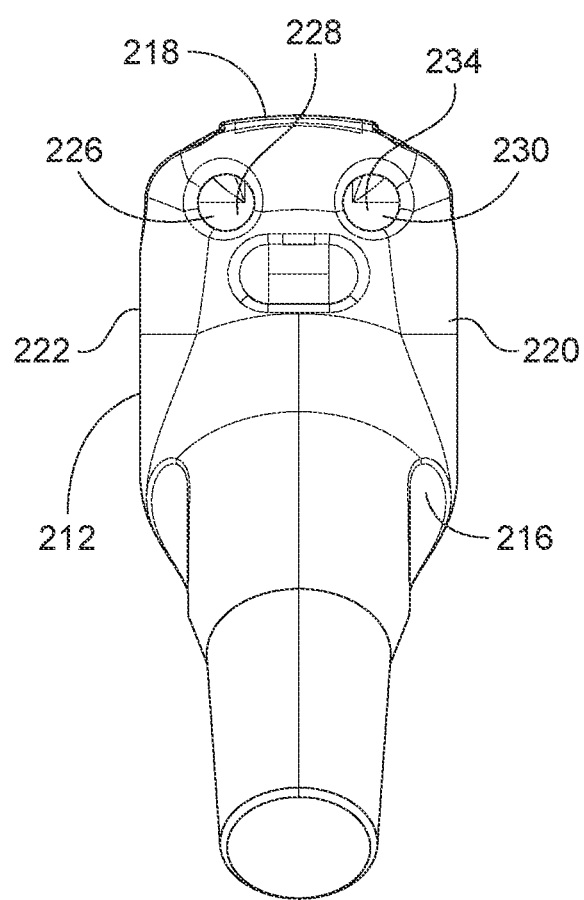
FIG. 4 is a top plan view thereof.
Figure 5:
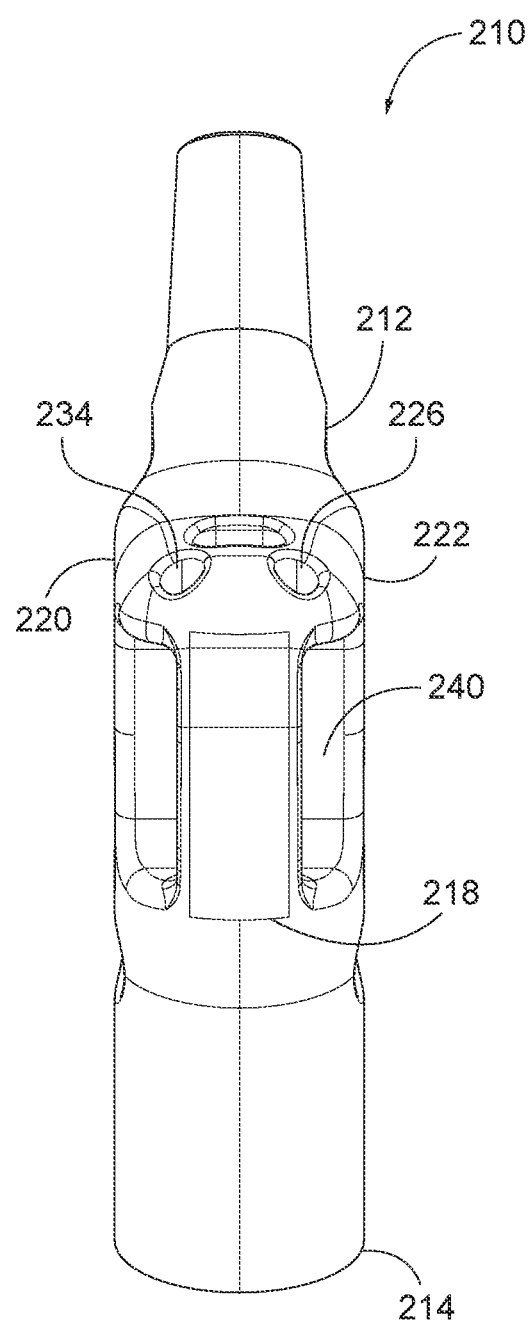
FIG. 5 is a rear elevation view thereof.
Figure 6:
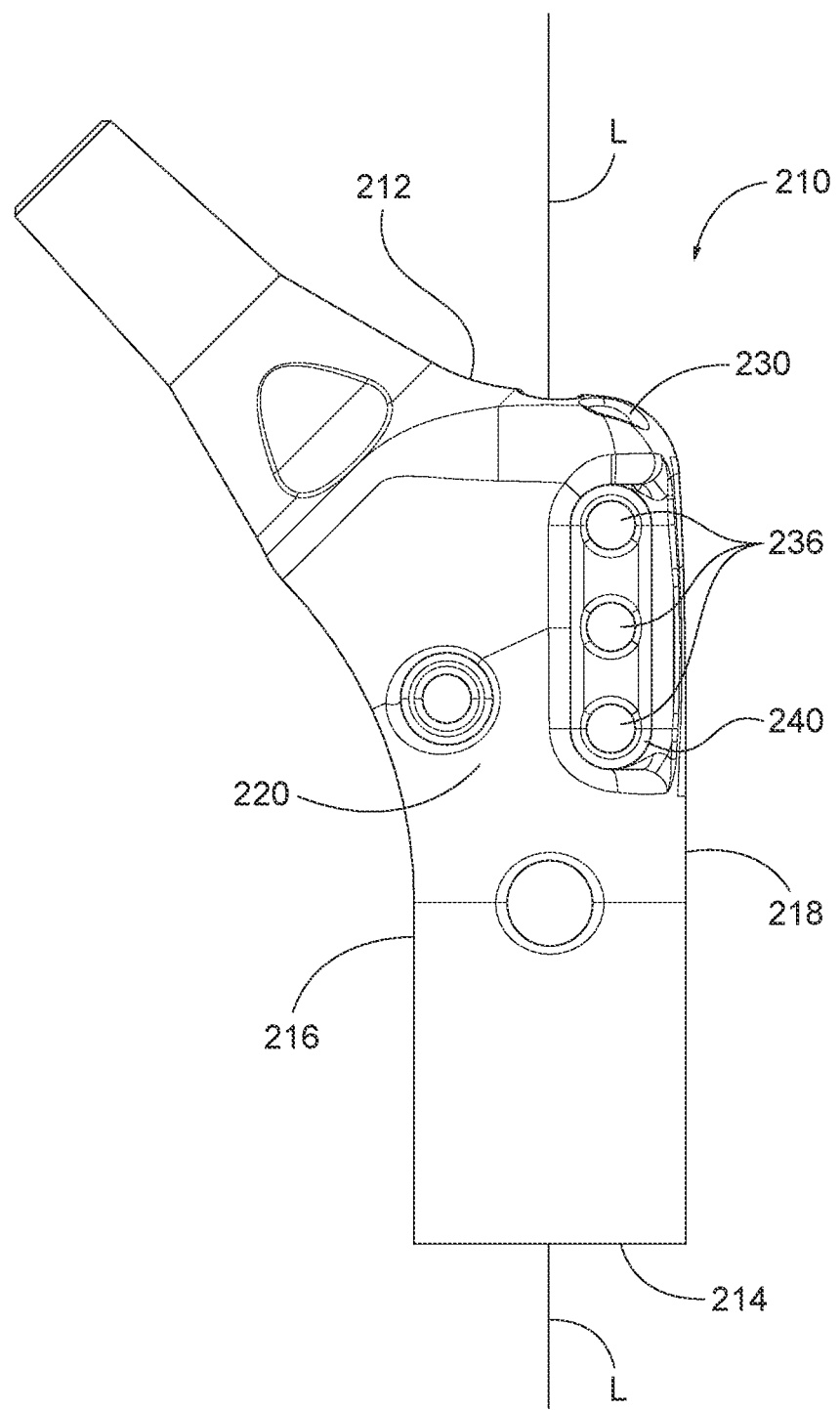
FIG. 6 is a left elevation view thereof.

Reference is now made to FIGS. 2A and 2B, which illustrate a proximal tibia implant 110 according to a second embodiment. The implant illustrated in FIGS. 2A and 2B is for a patient's left proximal tibia and the implant for a right proximal tibia, while not shown, is a mirror-image thereof. As illustrated in FIGS. 2A and 2B and further discussed below, the implant 110 includes suture bores 128, 134 that have an angled/diagonal, or skewed, orientation within the anatomical planes (lateral/sagittal and frontal/coronal). The suture bores have the skewed orientation so that the adjacent soft tissues (i.e., tendons or ligaments) can be advanced via the suture therethrough in superior-inferior and inferior-superior directions. Openings, or holes, at the ends of the suture bores are configured to approximate the adjacent associated soft tissue to the implant.

With continued reference to FIGS. 2A and 2B, the proximal tibia implant 110 includes a superior end 112, an inferior end 114 opposite the superior end 112, and a longitudinal axis L extending between the superior and inferior ends 112, 114. The implant 110 further includes a first (i.e., lateral or medial) side 116 extending between the superior and inferior ends 112, 114, and a second (i.e., medial or lateral), side 118 opposite the first side 116 and extending between the superior and inferior ends 112, 114. An anterior surface 120 extends between the superior and inferior ends 112, 114, and a posterior surface 122 extends between the superior and inferior ends 112, 114, opposite the anterior surface 120.

The proximal tibia implant 110 includes a plurality of suture holes. A first, suture hole 124 is formed in the first side 116 of the implant 110 between the superior and inferior ends 112, 114, and a second suture hole 126 is formed in the anterior surface 120 proximate the superior end 112 and first side 116. A first suture bore 128 is formed between the first and second suture holes 124, 126 and extends at a third acute angle $A_3$ with the longitudinal axis L in the lateral/sagittal plane (see FIG. 2A, in which an imaginary dashed line extends from the first suture bore 128 to help illustrate this angle), and extends at a fourth $A_4$ acute angle with the longitudinal axis L in the frontal/coronal plane (see FIG. 2B, in which an imaginary dashed line extends from the first suture bore 128 to help illustrate this angle). A third suture hole 130 is formed in the anterior surface 120 proximate the superior end 112 and second side 118, and a fourth suture hole 132 is formed in the second side 118 between the superior and inferior ends 112, 114. A second bore 134 is formed between the third and fourth suture holes 130, 132 and extends at the third acute angle $A_3$ with the longitudinal axis L in the lateral/sagittal plane, and extends at the fourth acute angle $A_4$ with the longitudinal axis L in the frontal/coronal plane.

In various embodiments, the third acute angle $A_3$ and fourth acute angle $A_4$ both range from 0° to 60° or from 10° to 40°. In a preferred embodiment, both the third acute angle $A_3$ and fourth acute angle $A_4$ range from 15° to 30°. In a more preferred embodiment, the third acute angle $A_3$ is 28.7°, and the fourth acute angle $A_4$ is 18°. The third acute angle $A_3$ and fourth acute angle $A_4$ are determined according to two criteria, namely, (1) an angle measurement that facilitates close alignment to the line of action of the soft tissue, and (2) an angle measurement that facilitates fitting the suture bore between other existing holes/features in the implant to avoid interference between the holes/features.

In the embodiments shown in FIGS. 2A and 2B the suture bores 128 and 134 have a diagonal, or skewed, orientation within the anatomical planes (lateral/sagittal and frontal/coronal). Other bore orientations (e.g., straight) are also possible and included in the scope of the invention. In various embodiments, the first and second bores 128, 134 can be curved if the implant 110 is cast or 3D-printed.

In various embodiments, the implant 110 includes additional suture holes. bores. In some embodiments, one or more suture bores 136 extend between the anterior surface 120 and posterior surface 122. The suture bores 136 are used to secure (i.e., clamp) the tissue T (i.e., tendons or ligaments) against the ingrowth/ongrowth surface(s) of the implant 110.

As illustrated in 2A and 2B, an exemplary surgical attachment method for securing the proximal tibia implant 110 within a patient includes the steps of (1) inserting the suture S up through the first suture hole 124 and the first bore 128 (see arrow pointing at an upward angle in FIG. 2B); (2) urging the suture S out of the second suture hole 126 so that the suture S is positioned proximate the adjacent soft tissue T (e.g., a tendon or ligament); (3) cross-stitching the suture S through and behind the adjacent soft tissue T; (4) inserting the suture S down through the third suture hole 130 and the second bore 134 (see arrow pointing at a downward angle in FIG. 2B); (5) urging the suture S out of the fourth suture hole 132; and (6) pulling the adjacent soft tissue T down (see arrow pointing straight down in FIG. 2B) and tying the suture S off proximate the anterior surface 120 of the proximal tibia implant 110. In various alternate embodiments, the suture S may be tied off at other locations. In various embodiments, the suture S may be reversed and run back through the bore(s) and soft tissue T a second time, and any number of additional times, to provide additional anchorage for the implant 110. In various embodiments, the order in which these steps are performed may vary. Other modifications of the method by a surgeon are also envisioned.

Referring again to FIGS. 1A, 1B, 2A and 2B, the suture bore geometries and methods of the present invention facilitate greater surface contact between the suture S and adjacent soft tissue T than the single band of typical surgical implants, suture holes and techniques. More particularly, the suture bore geometries and methods of the present invention enable the surgeon to form an X-shaped/crisscrossed pattern (see FIGS. 1B and 2B), similar to the orientation of a shoelace within a shoe, which provides greater surface contact between the suture S and soft tissue T, and also better/more evenly distributes stresses across the soft tissue.

Reference is now made to FIGS. 3-7B, which illustrate a proximal femur implant 210 as a third embodiment. The implant 210 as illustrated is for a patient's left proximal femur and the implant for a right proximal femur, while not shown, is a mirror-image thereof. The proximal femur implant 210 includes a superior end 212, an inferior end 214 opposite the superior end 212, and a longitudinal axis L extending between the superior and inferior ends 212, 214. The implant 210 further includes a first, or medial, side 216 extending between the superior and inferior ends 212, 214, and a second, or lateral, side 218 opposite the first side 216 and extending between the superior and inferior ends 212, 214. An anterior surface 220 extends between the superior and inferior ends 212, 214, and a posterior surface 222 extends between the superior and inferior ends 212, 214, opposite the anterior surface 220.

The proximal femur implant 210 includes first and second troughs 240 formed in the anterior surface 220 and posterior surface 222. The troughs 240 are further discussed below.

The proximal femur implant 210 includes a plurality of suture holes. Referring to FIGS. 3-7B, a first suture hole 224 is formed in the first trough 240 between the superior and inferior ends 212, 214. A second suture hole 226 is formed in the lateral side 218 proximate the superior end 212. A first suture bore 228 extends between the first and second suture holes 224, 226 at a first acute angle with the longitudinal axis in the frontal/coronal plane, and at a second acute angle with the longitudinal axis in the lateral/sagittal plane. A third suture hole 230 is formed in the lateral side 218 proximate the superior end 212. A fourth suture hole 232 is formed in the second trough 240 between the superior and inferior ends 212, 214. A second suture bore 234 extends between the third and fourth suture holes 230, 232 at the first acute angle with the longitudinal axis in the frontal/coronal plane, and at the second acute angle with the longitudinal axis in the lateral/sagittal plane.

Figure 7A:
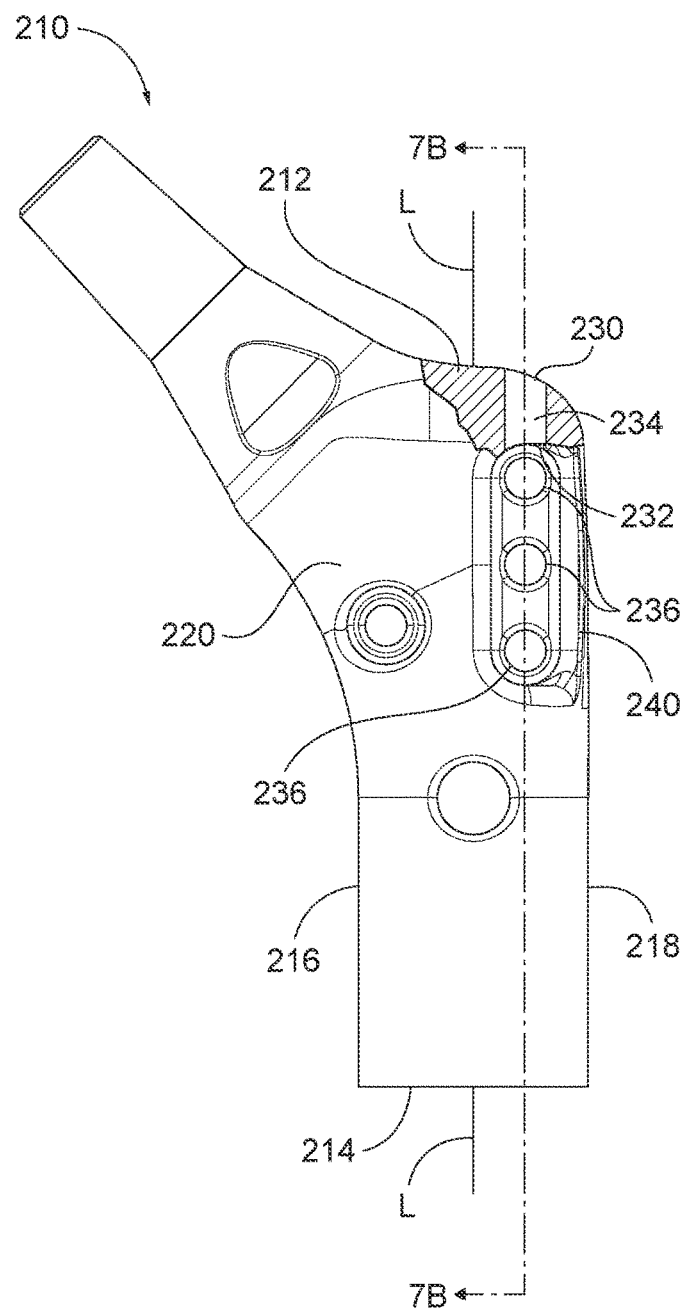
FIG. 7A is a left elevation view thereof with a portion removed to provide a partial sectional view.
Figure 7B:
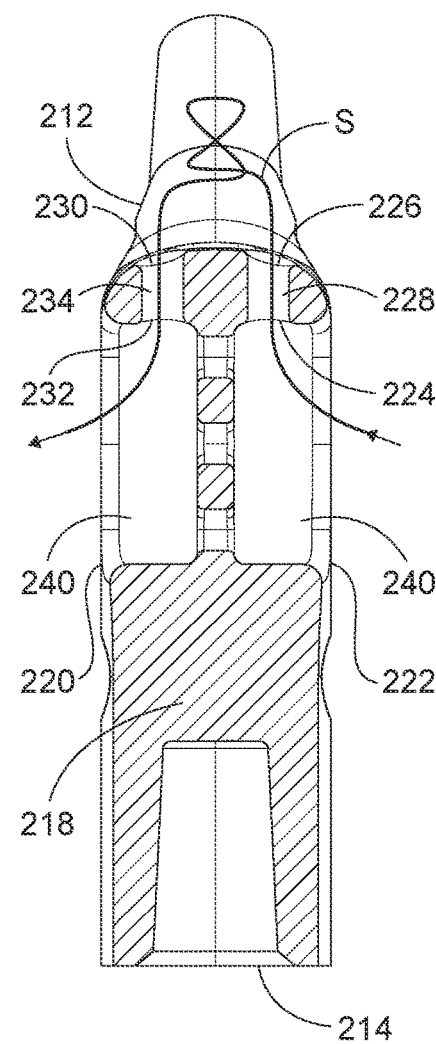
FIG. 7B is a cross-sectional view of the implant of FIG. 7A, taken along line 7B-7B.

As illustrated in FIGS. 7A and 7B, the first and second acute angles are V Thus, the first and second suture bores 228, 234 extend parallel to the longitudinal axis L, in a superior/inferior direction.

In various embodiments, the implant 210 includes additional suture bores, such as suture bores 236 formed between the first and second troughs 240 in the anterior and posterior surfaces 220 and 222. The troughs 240 decrease the length of the bores 236, which facilitates both manufacturing and cleaning. In other embodiments, the implant 210 does not include troughs, and the suture bores 236 are formed between the anterior and posterior surfaces 220 and 222 themselves (i.e., the end openings of the suture bores 236 are flush with the anterior and posterior surfaces 220 and 222).

An exemplary surgical attachment method for securing the proximal femur implant 210 within a patient includes same steps as described above in connection with the proximal femur implant 10.

The suture bore geometries and methods of the present invention allow the surgeon to optimally position and tighten the tissue against an implant surface during surgery, and subsequently provide a more ideal orientation of the tissue relative to the implant for optimal healing and functionality. The suture bore geometries and methods thereby provide a more ideal anchorage potential for biomechanical forces in limb salvage and orthopedic reconstruction.

The suture bore geometries and methods of the present invention enable the surgeon to advance/pull the suture downwardly, in an anatomical direction along the tissue's line of action as originally in the bone. This advantageously makes manipulation of the suture easier for the surgeon, as opposed to pulling the suture from the side, as disclosed in prior art implants and associated surgical methods.

The suture bore geometries and methods of the present invention enable the surgeon to optimally manipulate/position the tissue against an opposing smooth, integrated porous, or roughened surface treatment/coating on the implant and subsequently secure the tissue in opposition to the implant.

In various embodiments, the implants disclosed herein may be formed from any medically-acceptable/biocompatible material, including, but not limited to, metals, metal alloys, ceramics, plastics and polymers. Non-limiting examples of metals and metal alloys include CoCr (cobalt-chrome), titanium alloys and stainless steel. A non-limiting example of a polymer includes PEEK.

In various embodiments, the implants disclosed herein include an anti-microbial coating.

While proximal femur and proximal tibia implants and their respective suture hole geometries and methods have been disclosed herein, also included within the scope of the present invention are various embodiments of distal long bone implants, including, but not limited to, distal femur implants and distal tibia implants and the respective suture hole geometries and methods configured for such distal long bones.

In various embodiments, the implants, suture hole geometries and methods of the present invention may be used with other long bones (i.e., other than the femur and/or tibia). Such bones include, but are not limited to, the fibula, radius, humerus and/or ulna, or any other bones. In further various embodiments, the implants, suture hole geometries and methods of the present invention may be modified for use with other bones, such as those of the pelvis, skull, hand and foot.

In various embodiments, the suture bores may be formed in any plurality/number, and at various angles and positions. In various embodiments, the suture bores distally diverge and proximally converge to facilitate tissue attachment and manipulation, as described herein.

Modifications, additions, or omissions may be made to the systems, apparatuses, and methods described herein without departing from the scope of the disclosure. For example, the components of the systems and apparatuses may be integrated or separated. Moreover, the operations of the systems and apparatuses disclosed herein may be performed by more, fewer, or other components and the methods described may include more, fewer, or other steps. Additionally, steps may be performed in any suitable order. As used in this document, "each" refers to each member of a set or each member of a subset of a set.

Other embodiments of the invention will be apparent to those skilled in the art from consideration of the specification and practice of the invention disclosed herein. Although specific advantages have been enumerated above, various embodiments may include some, none, or all of the enumerated advantages. It is intended that the embodiments described above be considered as exemplary only, with a true scope and spirit of the invention being indicated by the appended claims. Moreover, none of the features disclosed in this specification should be construed as essential elements, and therefore, no disclosed features should be construed as being part of the claimed invention unless the features are specifically recited in the claims. In addition, it should be understood that any of the features disclosed on any particular embodiment may be incorporated in whole or in part on any of the other disclosed embodiments.

In any interpretation of the claims appended hereto, it is noted that no claims or claim elements are intended to invoke or be interpreted under 35 U.S.C. 112(f) unless the words "means for" or "step for" are explicitly used in the particular claim.

In general, any combination of disclosed features, components and methods described herein is possible. Steps of a method can be performed in any order that is physically possible.

All cited references are incorporated by reference herein.

Although embodiments have been disclosed, it is not desired to be limited thereby. Rather, the scope should be determined only by the appended claims.

While various embodiment of the present disclosure have been described in detail, it is apparent that modifications and alterations of those embodiments will occur to those skilled in the art. However, it is to be expressly understood that such modifications and alterations are within the scope and spirit of the present disclosure, as set forth in the following claims.

The foregoing discussion of the disclosure has been presented for purposes of illustration and description. The foregoing is not intended to limit the disclosure to the form or forms disclosed herein. In the foregoing Detailed Description for example, various features of the disclosure are grouped together in one or more embodiments for the purpose of streamlining the disclosure. This method of disclosure is not to be interpreted as reflecting an intention that the claimed disclosure requires more features than are expressly recited in each claim. Rather, as the following claims reflect, inventive aspects lie in less than all features of a single foregoing disclosed embodiment. Thus, the following claims are hereby incorporated into this Detailed Description, with each claim standing on its own as a separate preferred embodiment of the disclosure.

Moreover, though the present disclosure has included description of one or more embodiments and certain variations and modifications, other variations and modifications are within the scope of the disclosure, e.g., as may be within the skill and knowledge of those in the art, after understanding the present disclosure. It is intended to obtain rights which include alternative embodiments to the extent permitted, including alternate, interchangeable and/or equivalent structures, functions, ranges or steps to those claimed, whether or not such alternate, interchangeable and/or equivalent structures, functions, ranges or steps are disclosed herein, and without intending to publicly dedicate any patentable subject matter.

The invention claimed is:

1. An implant comprising:
a superior end;
an inferior end opposite the superior end;
a longitudinal axis extending between the superior and inferior ends;
a first side extending between the superior and inferior ends, the first side being a lateral a second side opposite the first side and extending between the superior and inferior ends, the second side being a medial side, the implant being a proximal femur implant;
an anterior surface extending between the superior and inferior ends;
a posterior surface opposite the anterior surface and extending between the superior and inferior ends;
a first suture hole between the superior and inferior ends;
a second suture hole proximate the superior end, the first suture hole being between the second suture hole and the inferior end; and
a first suture bore formed between the first and second suture holes, and extending between the first and second suture holes, and extending at a first acute angle with the longitudinal axis in a sagittal plane, and extending at a second acute angle with the longitudinal axis in a coronal plane;
a third suture hole proximate the superior end and the second suture hole;
a fourth suture hole between the third suture hole and the inferior end, the first suture hole being formed in the posterior surface between the superior and inferior ends, the second and third suture holes being formed in the first side proximate the superior end, and the fourth suture hole being formed in the anterior surface between the superior and inferior ends; and
a second suture bore formed between the third and fourth suture holes, and extending between the third and fourth suture holes, and extending at the first acute angle with the longitudinal axis in a sagittal plane, and extending at the second acute angle with the longitudinal axis in a coronal plane, the first suture bore and second suture bore converging in a direction toward the superior end.

2. The implant of claim 1, wherein the first acute angle and second acute angle are within a range of 0° to 60°.

3. The implant of claim 1, wherein the first acute angle and second acute angle are within a range of 10° to 40°.

4. The implant of claim 1, wherein the first acute angle and second acute angle are within a range of 15° to 30°.

5. The implant of claim 1, further comprising at least one third suture bore formed between the anterior and posterior surfaces.

6. The implant of claim 1, further comprising a first trough formed in the posterior surface and a second trough formed in the anterior surface, wherein the first suture hole is formed in the first trough between the superior and inferior ends, the second and third suture holes are formed in the lateral side proximate the superior end, and the fourth suture hole is formed in the second trough between the superior and inferior ends.

7. The implant of claim 6, further comprising at least one third suture bore formed between the first and second troughs.

8. The implant of claim 7, wherein the at least one third suture bore formed between the anterior and posterior surfaces.

9. The implant of claim 1, further comprising an antimicrobial coating.

10. The implant of claim 1, wherein the implant is formed from a material selected from the group consisting of metals, metal alloys, polymers, plastics and ceramics.

11. An implant comprising: a superior end;
an inferior end opposite the superior end;
a longitudinal axis extending between the superior and inferior ends; a first side extending between the superior and inferior ends;
a second side opposite the first side and extending between the superior and inferior ends;
an anterior surface extending between the superior and inferior ends;
a posterior surface opposite the anterior surface and extending between the superior and inferior ends;
a first suture hole between the superior and inferior ends;
a second suture hole proximate the superior end, the first suture hole being between the second suture hole and the inferior end; and
a first suture bore formed between the first and second suture holes, and extending between the first and second suture holes, and extending at a first acute angle with the longitudinal axis in a sagittal plane, and extending at a second acute angle with the longitudinal axis in a coronal plane.

12. The implant of claim 11, further comprising:
a third suture hole proximate the superior end and the second suture hole;
a fourth suture hole between the third suture hole and the inferior end; and
a second suture bore formed between the third and fourth suture holes and extending at the first acute angle with the longitudinal axis in the sagittal plane, and extending at the second acute angle with the longitudinal axis in the coronal plane.

13. The implant of claim 12, wherein the implant is a proximal femur implant, the first side is a lateral side and the second side is a medial side.

14. The implant of claim 13, wherein the first suture hole is formed in the posterior surface between the superior and inferior ends, the second and third suture holes are formed in the first side proximate the superior end, and the fourth suture hole is formed in the anterior surface between the superior and inferior ends.

15. The implant of claim 14, further comprising at least one third suture bore formed at a location.

16. The implant of claim 13, further comprising a first trough formed in the posterior surface and a second trough formed in the anterior surface, wherein the first suture hole is formed in the first trough between the superior and inferior ends, the second and third suture holes are formed in the lateral side proximate the superior end, and the fourth suture hole is formed in the second trough between the superior and inferior ends.

* * * * *